(12) United States Patent
Lai et al.

(10) Patent No.: US 8,931,900 B2
(45) Date of Patent: Jan. 13, 2015

(54) METHOD AND APPARATUS FOR DETERMINING DEPTH OF FOCUS OF AN EYE OPTICAL SYSTEM

(71) Applicant: Bausch & Lomb Incorporated, Rochester, NY (US)

(72) Inventors: Ming Lai, Dublin, CA (US); Ian G. Cox, Honeoye Falls, NY (US); Paul D. Ludington, Brockport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 13/655,048

(22) Filed: Oct. 18, 2012

(65) Prior Publication Data
US 2014/0111764 A1    Apr. 24, 2014

(51) Int. Cl.
| A61B 3/00 | (2006.01) |
|---|---|
| A61B 3/08 | (2006.01) |
| A61B 3/032 | (2006.01) |
| A61B 3/09 | (2006.01) |
| A61B 3/103 | (2006.01) |

(52) U.S. Cl.
CPC . *A61B 3/08* (2013.01); *A61B 3/032* (2013.01); *A61B 3/09* (2013.01); *A61B 3/103* (2013.01)
USPC .......................................... 351/201; 351/200

(58) Field of Classification Search
CPC ............ A61B 3/14; A61B 3/102; A61B 3/12; A61B 3/008; A61B 3/024; A61B 3/0091; A61B 3/032; A61B 3/113; A61B 3/11; A61B 3/1173; A61B 5/0059; A61B 5/0066; G01B 9/02043; G01B 9/02083; G01J 9/00
USPC ......... 351/201, 203, 200, 205, 206, 211, 212, 351/221, 222, 23, 236
See application file for complete search history.

(56) References Cited

U.S. PATENT DOCUMENTS

| 4,533,221 A * | 8/1985 | Trachtman ..................... 351/203 |
|---|---|---|
| 4,997,269 A | 3/1991 | Cushman |
| 5,223,866 A | 6/1993 | Cushman |
| 6,382,795 B1 * | 5/2002 | Lai ................................ 351/212 |
| 6,739,722 B2 | 5/2004 | Laguette et al. |
| 7,963,654 B2 | 6/2011 | Aggarwala |
| 2012/0075585 A1 | 3/2012 | Dorronsoro Diaz et al. |

FOREIGN PATENT DOCUMENTS

| GB | 2134281 A | 8/1984 |
|---|---|---|
| GB | 2148534 A | 5/1985 |
| WO | 91/12764 | 9/1991 |

OTHER PUBLICATIONS

C.o Mutti et al: "AC/A ratio, age, and refractive error in children", American Journal of Opthalmology, vol. 41, No. 9, Aug. 1, 2000, pp. 2469-2478, XP055090514, ISSN: 0002-9394, DOI: 10.1016/S0002-9394(00)00760-1.*

(Continued)

*Primary Examiner* — William Choi
*Assistant Examiner* — Sharrief Broome
(74) *Attorney, Agent, or Firm* — Toan P. Vo

(57) ABSTRACT

A device for measuring depth of field of an eye optical system that includes a lens Badal having positive optical power, a positioning apparatus adapted to maintain the eye optical system on the image side of the lens at a first focal plane of the lens and a multi-vergency target that provides a plurality of objects that are simultaneously viewable, through the lens, by the eye optical system.

13 Claims, 2 Drawing Sheets

(56) References Cited

OTHER PUBLICATIONS

International Search Report and Written Opinion of the International Searching Authority in corresponding PCT Application No. PCT/US2013/056808 dated Nov. 28, 2013 (10 pages).

Mutti et al: AC/A Ratio, Age, and Refractive Error in Children—American Journal of Ophthalmology, vol. 41, No. 9, Aug. 1, 2000, pp. 2469-2478, XP055090514, Issn: 0002-9394 (10 pages).

* cited by examiner

METHOD AND APPARATUS FOR DETERMINING DEPTH OF FOCUS OF AN EYE OPTICAL SYSTEM

FIELD OF INVENTION

The present invention relates to devices for measuring depths of field of eye optical systems.

BACKGROUND OF THE INVENTION

It is desirable to measure the depth of field of an eye optical system. Such measurements can be used by lens designers to understand performance of an eye optical system or by ophthalmic patients (or potential patients) to understand performance of a lens or refractive procedure. Patients and potential patients interested in eye optical systems that provide presbyopic solutions are particularly interested in the depth of field that can be regained by a given lens or procedure, such as depth of field gains generated by using a presbyopic solution such as a multifocal lens. Eye care practitioners may measure a patient's base-line depth of focus (i.e., prior to implementation of a presbyopic solution) for comparison to the depth of field that is attained after implementation of the presbyopic solution to understand the improvement provided by the presbyopic solution.

Conventional techniques for measuring depth of field have included scanning a target within the object space of the lens while images of the object are observed. Such measurement techniques have had shortcomings due to amount of the practitioner's and wearer's time that is consumed to perform a measurement, and also because the characteristics of the eye optical system may change over the time span during which the measurement is made (e.g., tear film may evaporate or otherwise change, the degree of accommodation may change) thereby yielding less accurate results.

SUMMARY

Aspects of the present invention are directed to a device for measuring depth of field of an eye optical system, comprising a lens Badal having positive optical power, a positioning apparatus adapted to maintain the eye optical system on the image side of the lens at a first focal plane of the lens, and a multi-vergency target that provides a plurality of objects that are simultaneously viewable, through the lens, by the eye optical system.

In some embodiments, at least one of the plurality of objects is proximate a second focal plane of the lens. In some embodiments, the device further comprising reflective surfaces to reflect the plurality of objects into the field of view of the eye optical system.

The eye optical system may comprise a human eye.

In some embodiments, the positioning apparatus comprises a chin rest or a viewing aperture.

The plurality of objects may be self-illuminated. In some embodiments, the plurality of objects is formed in a one-dimensional array extending through the depth of field of the eye optical system.

Each of the plurality of objects may have a corresponding prism or mirror to reflect the object into the field of view of the eye optical system, perpendicular to the optical axis.

In some embodiments, the optical path differences between the plurality of objects are uniform with respect to the eye optical system. The optical path differences between the plurality of objects, as perceived by the eye optical system, may be one diopter.

In some embodiments, the plurality of objects are formed in a two-dimensional array, a first dimension of the array extending through the depth of field of the eye optical system, and a second dimension of the array having letters corresponding to different acuities than one another.

The plurality of objects may be generated by multiply reflecting a first object from two reflective surfaces to generate a plurality of virtual objects.

The device may be a binocular system.

The term "eye optical system" as used herein refers to an optical system such as a natural eye or an optical system that includes an eye and an ophthalmic optical correction or a simulation of an ophthalmic optical correction. The term "eye optical system" also refers to model eyes corresponding to a natural eye or a model eye that contains an ophthalmic optical correction or a simulation thereof. For example, a simulation of an ophthalmic correction may be achieved using a phase plate located in front of the eye. It will be appreciated that use of such a simulation may be particularly advantageous prior to use of an ophthalmic correction that requires surgical intervention.

The term "ophthalmic optical correction" as used herein refers to an ophthalmic lens, an optical feature of an eye that has been refractively corrected or other ophthalmically-modified features of an eye optical system. For example, an optical feature of an eye that has been refractively corrected may include a crystalline lens or cornea that has been reshaped or otherwise optically modified using a mechanical or optical technique (e.g., LASIK or change of index of refraction).

The term "focal plane" refers to a plane located one focal length from a principal plane. A lens has two focal planes. A first (or front) focal plane on an object side of a lens and a second (or rear) focal plane on the image side of a lens. For example, the rear focal plane is located one focal length from the rear principal plane.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Figure 1A:
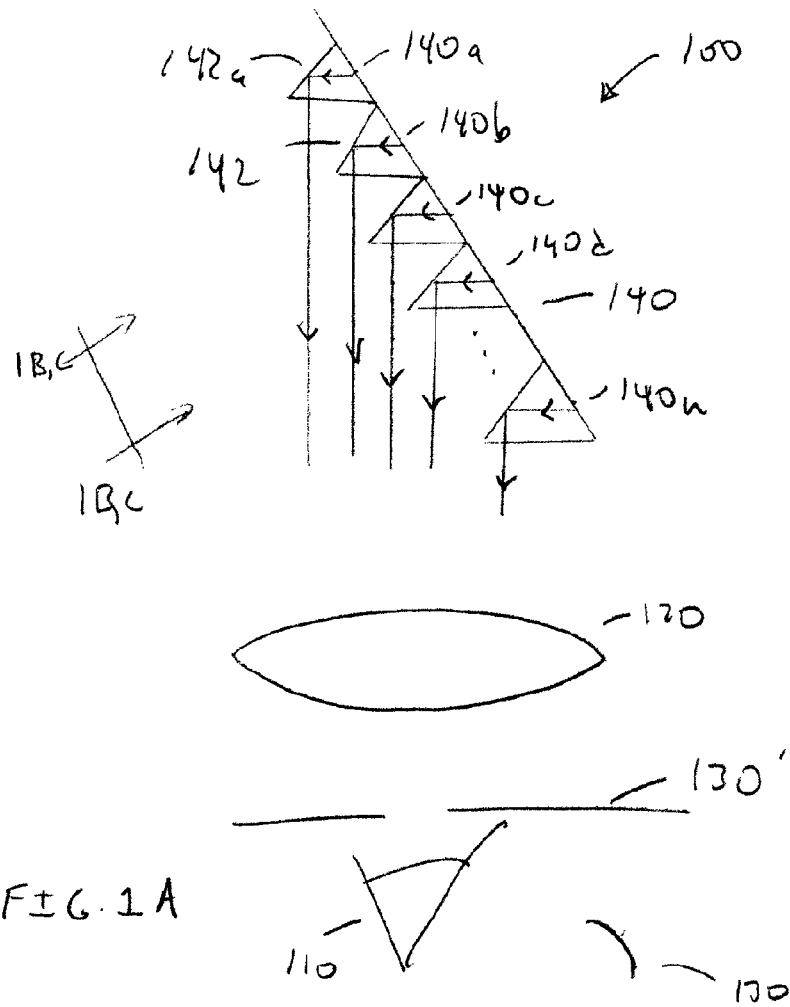
FIG. 1A is a schematic illustration of an embodiment of a device for measuring depth of field of an eye optical system according to aspects of the invention.

FIG. 1A is a schematic illustration of an embodiment of a device 100 for measuring depth of field of an eye optical system 110 according to aspects of the invention. The device comprises a lens 120 having positive optical power, a positioning apparatus 130 and/or 130' to maintain the eye optical system at a first focal plane of the lens, and a multi-vergency target 140 comprising objects 140a-140n.

Lens 120 and positioning apparatus 130 operate together to form a Badal system with lens 120 and eye optical system 110 such that uniform differences in distances on the object side of the lens correspond to linear differences in dioptric power for eye optical system 110. The lens may be any suitable positive lens that does not substantially alter the perceived optical quality of the eye optical system and permits for a suitable size of device 100. Typically, a Badal lens is a simple lens comprising one or two lens elements.

Positioning apparatus 130 may take any suitable form to facilitate placement of eye optical system 110 at or near the focal plane of the lens. For example, in the embodiments where the eye optical system is a human eye, positioning apparatus may comprise a chin rest 130 to position a patient's eye and/or a viewing aperture 130' to position a patient's eye such that objects 140a-140n with uniform optical path length distances between them correspond to images having linear differences in dioptric power of eye optical system 110. Alternatively, if the eye optical system 140 includes a model eye comprising an electronic sensor that operates as in the manner of a retina, the positioning apparatus may comprise mechanical components that appropriately position the model eye to achieve a Badal system. It will be appreciated that an appropriate system is one that places the model eye such that uniform optical path length distances between objects 140a-140n correspond to linear differences in dioptric power of eye optical system 110.

The multi-vergency target 140 provides a plurality of objects 140a-140n at different optical distances from the lens on the object side of the lens. The target 140 is typically located proximate the focal plane of the lens so that at least one of the objects 140a-140n is located proximate a second focal plane and said object appears, to the eye optical system, to be at infinity. However, the location at which the target (and objects) are located is determined by the measurements of the eye optical system that are to be made. It will be understood that, if the target is made to straddle the focal plane, some objects would appear in hyperopic space and other objects would appear in myopic space. The expression "proximate a focal plane" means within one-half of a diopter of the focal plane and, in some instances, within one-quarter of a diopter of the focal plane.

Each of the plurality of objects 140a-140n includes an identifiable object having a variety of spatial frequencies, such as characters or images. It will be appreciated that the plurality of objects are simultaneously viewable by eye optical system 110. That is, objects 140a-140n exist within the field of view of the eye optical system.

Objects 140a-140n may be illuminated with ambient light or by illumination projected on the front or back of the objects. In some embodiments, the objects are self-illuminated, for example the objects may be formed by LEDs which can be selectively activated to provide the objects.

Figure 1B:
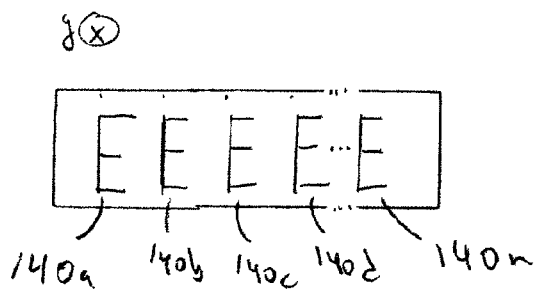
FIG. 1B is a schematic illustration of an embodiment of objects for use in the device of FIG. 1A viewed along lines 1B,C-1B,C, where the objects form a one-dimensional array.

As shown in FIG. 1B, in an embodiment, objects 140a-140n form a one-dimensional array, extending through the depth of field of eye optical system 110 at an angle (e.g., 30 degrees) with the optical axis. Typically the objects are identical to one another; however the objects may be different than one another. It will also be appreciated that, an advantageous characteristic of a Badal system as used in the present invention, is that, even though the objects are caused to be at different vergencies, each of the objects will maintain the same angular resolution when observed by the eye optical system.

Each object has a corresponding prism 142a-142n (e.g., an equilateral prism) that totally internally reflects the object into the field of view of the eye optical system, normal to the optical axis. In some embodiments, correspondingly-positioned silvered mirror may be used instead of the prisms to reflect the objects into the field of view.

Reflective configurations as described above have advantages if the objects are to be illuminated from the rear or if the objects are formed by self-illumination, and for facilitating alignment of the system. However, it will be appreciated that the objects themselves can be located in the field of the view normal to the optical axis without reflection, such as on a staircase-shaped apparatus.

It will be appreciated that the vergencies of the objects depends on separation of the objects along the viewing axis and focal length of lens 120. It will also be appreciated that if the optical path distances between objects 140a-140n are uniform that an amount of depth of field of the eye optical system 110 can be determined by counting the number of objects that are discernible by the eye optical system and multiplying the result by the dioptric distance between the objects (as perceived the eye the optical system) to determine the depth of field. If the distances are selected to correspond to one diopter separations, the number of diopters of depth of field that the eye optical system is capable of generating is equal to the number of objects that are discernible.

Figure 1C:
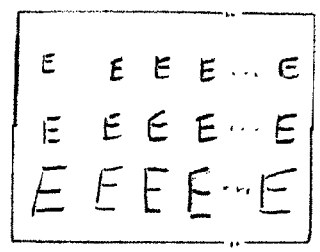
FIG. 1C is a schematic illustration of an embodiment of objects for use in the device of FIG. 1A viewed along lines 1B,C-1B,C, where the objects form a two-dimensional array.

As shown in FIG. 1C, in some embodiments, the array of letters is two-dimensional such that, at each object distance, a plurality of letters are present along a second dimension, such that a depth of field can be determined for each of a plurality of acuities (e.g., 20/20, 20/40, 20/60). It will be appreciated that the prisms 142a-142n have lengths sufficient to reflect objects of all acuities (at each given object distance) into the field of view of eye optical system 110.

Figure 2:
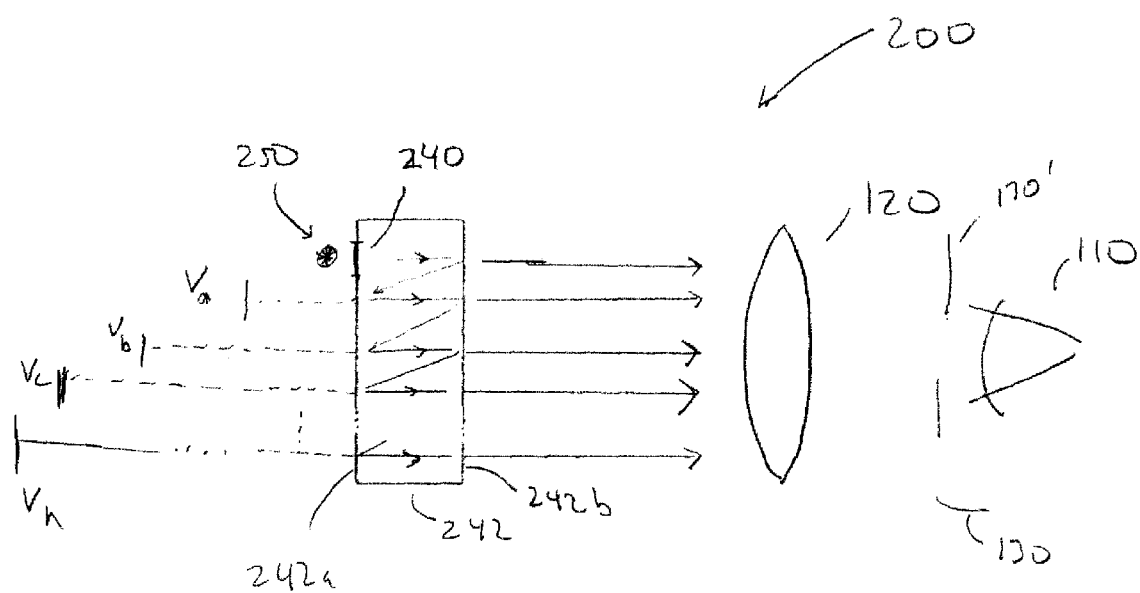
FIG. 2 is a schematic illustration of another embodiment of a device for measuring depth of field of an eye optical system according to aspects of the invention.

FIG. 2 is a schematic illustration of another embodiment of a device 200 for measuring depth of field of an eye optical system 110 according to aspects of the invention. Device 200 operates in a manner similar to device 100 other than generation of the multiple objects at different object distances (i.e., different vergencies).

In device 200, a multi-vergency target comprises a single object 240 that is multiply reflected from two reflective surfaces 242a, 242b (e.g., parallel mirrors) which may be formed on the surfaces of a plate of glass 242. The reflective surfaces have suitable reflectivities (e.g., reflectivity of surface 242a equals 100% and the reflectivity of surface 242b equals 91%) to generate a plurality of objects (virtual objects $V_a$-$V_n$) which are generated from multiple reflections form the surfaces, and are in addition to objects 240. It will be appreciated that the reflective surfaces operate to reflect a plurality o objects into the field of view of the eye optical system. It will be appreciated that the objects 240, $V_a$-$V_n$ appear to have different vergencies (i.e., object distances) when viewed by the eye optical system and, as in FIG. 1A, lens 120 and positioning apparatus 130 operate together to form a Badal system with lens 120 and eye optical system 110 such that uniform differences in object distance on the object side of the lens correspond to linear differences in dioptric power for eye optical system 110.

In device 200 rear illumination of object 240 is provided by a light source 205. The intensity of light source 205 is selected such that the objects seen by eye optical system 110 have suitable brightness to allow images of suitable brightness to be observed.

It will also be appreciate that, although the above devices were shown as being adapted for measurement of a single eye, and therefore are viewed with monocular vision, a device may be configured to permit both of a viewer's eyes to view a multi-vergency target (i.e., binocular measurements). The device may be configured to permit both eyes to view a same target using appropriate steering optics or separate targets (e.g., with two Badal systems). In binocular devices, it may be advantageous that the optical pathway for one eye or both eyes be rotationally adjustable to permit proper fusing of the objects by the viewer.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A device for measuring a depth of field of an eye optical system, comprising:
    a lens Badal having a positive optical power;
    a positioning apparatus adapted to maintain the eye optical system on the image side of the lens Badal at a first focal plane of the lens Badal; and
    a multi-vergency target including a plurality of objects located at different optical distances from the lens Badal and simultaneously viewable at a common angular resolution, through the lens Badal, by the eye optical system.

2. The device of claim 1, wherein the plurality of objects straddles a second focal plane of the lens Badal on an object side of the lens Badal.

3. The device of claim 1, further comprising reflective surfaces to reflect the plurality of objects into the field of view of the eye optical system.

4. The device of claim 1, wherein the eye optical system comprises a human eye.

5. The device of claim 1, wherein the positioning apparatus comprises a chin rest or a viewing aperture.

6. The device of claim 1, wherein the plurality of objects are self-illuminated.

7. The device of claim 1, wherein the plurality of objects are formed in a one-dimensional array extending through the depth of field of the eye optical system.

8. The device of claim 7, wherein each of the plurality of objects has a corresponding prism or mirror to reflect the object into the field of view of the eye optical system, perpendicular to the optical axis.

9. The device of claim 1, wherein optical path differences between the plurality of objects is uniform with respect to the eye optical system.

10. The device of claim 9, wherein the optical path differences between the plurality of objects is one diopter.

11. The device of claim 1, wherein the plurality of objects are formed in a two-dimensional array, a first dimension of the array extending through the depth of field of the eye optical system, and a second dimension of the array having letters corresponding to different acuities than one another.

12. The device in claim 1, wherein the plurality of objects is generated by multiply reflecting a first object from two reflective surfaces to generate a plurality of virtual objects.

13. The device of claim 1, wherein the device is a binocular system.

* * * * *